(12) United States Patent
Kehoe et al.

(10) Patent No.: US 11,583,286 B2
(45) Date of Patent: Feb. 21, 2023

(54) IMPLANT SYSTEM COMPRISING A DELIVERY WIRE ASSEMBLY AND AN IMPLANT

(71) Applicant: Clearstream Technologies Limited, Enniscorthy (IE)

(72) Inventors: James Kehoe, Enniscorthy (IE); Dónal McDonagh, Dublin (IE); John O'Shea, Wexford (IE)

(73) Assignee: Clearstream Technologies Limited, Enniscorthy (IE)

( * ) Notice: Subject to any disclaimer, the term of this patent is extended or adjusted under 35 U.S.C. 154(b) by 38 days.

(21) Appl. No.: 16/638,667

(22) PCT Filed: Aug. 17, 2018

(86) PCT No.: PCT/EP2018/072360
§ 371 (c)(1),
(2) Date: Feb. 12, 2020

(87) PCT Pub. No.: WO2019/034787
PCT Pub. Date: Feb. 21, 2019

(65) Prior Publication Data
US 2021/0219985 A1 Jul. 22, 2021

(30) Foreign Application Priority Data
Aug. 18, 2017 (GB) .................................... 1713329

(51) Int. Cl.
*A61B 17/12* (2006.01)
(52) U.S. Cl.
CPC .. *A61B 17/12145* (2013.01); *A61B 17/12109* (2013.01); *A61B 2017/12095* (2013.01)

(58) Field of Classification Search
CPC ........ A61B 17/12145; A61B 17/12109; A61B 2017/12095; A61B 2017/12054; A61F 2002/9505
See application file for complete search history.

(56) References Cited

U.S. PATENT DOCUMENTS 7,237,552 B2 * 7/2007 Khera ...................... A61F 6/225
128/830
8,690,935 B2 4/2014 Tenne
(Continued)

FOREIGN PATENT DOCUMENTS

CN 1630496 A 6/2005
EP 1212018 B1 12/2010
(Continued)

OTHER PUBLICATIONS

Examination Report dated Jun. 30, 2021 pertaining to New Zealand Patent Application No. NZ761135.
(Continued)

*Primary Examiner* — Robert A Lynch
*Assistant Examiner* — Mikail A Mannan
(74) *Attorney, Agent, or Firm* — Dinsmore & Shohl LLP

(57) ABSTRACT

There is provided an implant system comprising: a delivery wire assembly having a female detachment mechanism component; and an implant having a male detachment mechanism component, wherein the female detachment mechanism component comprises a coil configured to receive the male detachment mechanism component such that the male detachment mechanism component is attachable to the female detachment mechanism component.

18 Claims, 5 Drawing Sheets

(56) References Cited

U.S. PATENT DOCUMENTS

2013/0296915 A1\* 11/2013 Bodewadt ........ A61B 17/12113
606/200
2016/0166257 A1\* 6/2016 Allen ............... A61B 17/12113
606/200

FOREIGN PATENT DOCUMENTS

| JP | 2003516774 A | 5/2003 |
|----|--------------|--------|
| WO | 0113832 A1 | 3/2001 |
| WO | 2009/135934 A1 | 11/2009 |

OTHER PUBLICATIONS

Search Report dated Feb. 21, 2018 pertaining to United Kingdom Patent Application No. GB1713329.9.
International Search Report and Written Opinion dated Dec. 10, 2018 pertaining to International PCT Application No. PCT/EP2018/072360.
Japanese Office Action dated Jun. 17, 2022 pertaining to JP Patent Application No. 2020-506115 filed Feb. 17, 2020 pp. 1-5.
Office Action dated Dec. 1, 2022, pertaining to Chinese application 201880053489.5.

\* cited by examiner

IMPLANT SYSTEM COMPRISING A DELIVERY WIRE ASSEMBLY AND AN IMPLANT

CROSS-REFERENCE TO RELATED APPLICATIONS

The present application is a national phase entry of International Application No. PCT/EP2018/072360, filed Aug. 17, 2018, which claims the benefit of priority to GB application No. 1713329.9, filed Aug. 18, 2017, the entireties of which are incorporated by reference herein.

TECHNICAL FIELD

The present disclosure relates to an implant system. Specifically, the present disclosure relates to an implant system comprising a delivery wire assembly and an implant.

BACKGROUND

Typically, implants which are to be delivered using a delivery wire are translated through a bodily lumen by the manipulation of a delivery wire connected to the implant. Once the implant has been correctly positioned within the body, the delivery wire is disconnected from the implant and removed, thereby leaving the implant in the deployed location. The delivery wire is connected to the implant by a detachment mechanism which can be selectively operated to disconnect the delivery wire from the implant.

As the diameters of the bodily lumens through which the delivery wire and implant are translated tend to be small, it is desired that the diameters of the delivery wire and implant are as small as possible. In the known devices, the detachment mechanism may contribute significantly to the overall diameter of the implant and delivery wire during insertion.

Accordingly, there is a need for an improved implant system in which the diameter of the detachment mechanism is reduced.

SUMMARY

In a first aspect of the present disclosure, there is provided an implant system comprising a delivery wire assembly having a female detachment mechanism component. The implant system further comprises an implant having a male detachment mechanism component. The female detachment mechanism component comprises a coil configured to receive the male detachment mechanism component such that the male detachment mechanism component is attachable to the female detachment mechanism component.

In one embodiment, the male detachment mechanism component is configured to be attached to the female detachment mechanism component by a relative rotation between the male detachment mechanism component and the female detachment mechanism component.

In one embodiment, the male detachment mechanism component comprises an external thread configured to mate with an internal thread formed by the coil of the female detachment mechanism component.

In one embodiment, the male detachment mechanism component is configured to mate with an internal thread formed by the coil of the female detachment mechanism component.

In one embodiment, the male detachment mechanism component is configured to be received within a central portion (or lumen) of the coil of the female detachment mechanism component.

In one embodiment, the female detachment mechanism component has only one coil.

In one embodiment, the coil of the female detachment mechanism is disposed on the central axis of the female detachment mechanism.

In one embodiment, the axis of the coil of the female detachment mechanism is coaxial with the axis of the delivery wire.

In one embodiment, the coil is a coil spring.

In one embodiment, the female detachment mechanism component further comprises a cylinder defining an internal bore, and wherein the coil is disposed within the internal bore of the cylinder.

In one embodiment, the female detachment mechanism component further comprises a cylinder defining an internal bore, and wherein the coil is disposed fully or partially within the internal bore of the cylinder.

In one embodiment, the coil abuts the surface of the internal bore along at least a portion of the length of the coil.

In one embodiment, the coil abuts the surface of the internal bore along the entire length of the coil.

In one embodiment, at least a portion of the coil is free to translate in along the length of the internal bore.

In one embodiment, one end of the coil is fixed to the cylinder.

In one embodiment, the one end of the coil is fixed to an end of the internal bore.

In one embodiment, one end of the internal bore is closed and another end of the internal bore is open.

In one embodiment, the another end of the internal bore is for receiving the male detachment mechanism component.

In one embodiment, one end of the coil is fixed to the another end of the internal bore.

In one embodiment, at least a portion of one end of the coil is disposed over a mandrel.

In one embodiment, the mandrel extends along at least a portion of the length of the internal bore of the cylinder.

In one embodiment, the mandrel extends from the closed end of the internal bore.

In one embodiment, the female detachment mechanism includes a viewing window. The viewing window may be configured to allow a user to determine whether the male detachment mechanism has been correctly received within and/or is being removed from the female detachment mechanism. The viewing window may be laser-cut into the female detachment mechanism.

In one embodiment, the female detachment mechanism includes a viewing window. The viewing window may be defined in the cylinder of the female detachment mechanism. The viewing window may be configured to allow a user to view the internal bore of the cylinder. The viewing window may be configured to allow a user to determine whether the male detachment mechanism has been received within and/or is being removed from the female detachment mechanism. The viewing window may be laser-cut into the cylinder of the female detachment mechanism.

In one embodiment, the male detachment mechanism component comprises two, three or more wires twisted together.

In one embodiment, the two, three or more wires are twisted together along at least part of their length.

In one embodiment, each wire of the two, three or more wires twisted together forms a helix with an axis coaxial with the axis of the helix formed by the other wire(s).

In one embodiment, the handedness of each of the helixes is the same.

Throughout this disclosure, 'handedness' refers to the direction of twists of a helix or twisted wire.

In one embodiment, the handedness of each of the helixes is right-handed or left-handed.

In one embodiment, the pitch of each helix is the same.

In one embodiment, the outer surface of the two, three or more wires twisted together defines an external thread configured to mate with an internal thread formed by the coil of the female detachment mechanism component.

In one embodiment, a pitch of the coil of the female detachment mechanism component is an integer multiple of a pitch of the two, three or more wires twisted together In one embodiment, a pitch of the coil of the female detachment mechanism component is one, two, three, four or five times a pitch of the two, three or more wires twisted together.

In one embodiment, the pitch of the two, three or more wires twisted together is constant In one embodiment, pitch of the coil of the female detachment mechanism component is constant.

In one embodiment, the two, three or more wires twisted together form a part of the core of the implant.

In one embodiment, the core is a central core of the implant. The central core may be disposed on the central axis of the implant.

In one embodiment, the handedness of the two, three or more wires twisted together is the same as the handedness of the coil of the female detachment mechanism component.

In one embodiment, the handedness of the two, three or more wires twisted together is opposite to the handedness of the coil of the female detachment mechanism component.

In one embodiment, the handedness of each of the two, three or more wires twisted together is the same as the handedness of the coil of the female detachment mechanism component.

In one embodiment, the handedness of each of the two, three or more wires twisted together is opposite to the handedness of the coil of the female detachment mechanism component.

In one embodiment, the male detachment mechanism component comprises a coil.

In one embodiment, the outer surface of the coil defines an external thread configured to mate with an internal thread formed by the coil of the female detachment mechanism component.

In one embodiment, the handedness of the coil of the female detachment mechanism component is the same as the handedness of the coil of the male detachment mechanism component.

In one embodiment, the handedness of the coil of the female detachment mechanism component is opposite to the handedness of the coil of the male detachment mechanism component.

In one embodiment, a pitch of the coil of the female detachment mechanism component is an integer multiple of a pitch of the coil of the male detachment mechanism component.

In one embodiment, a pitch of the coil of the female detachment mechanism component is one, two, three, four or five times the pitch of the coil of the male detachment mechanism component.

In one embodiment, the pitch of the coil of the male detachment mechanism component is constant.

In one embodiment, the pitch of the coil of the female detachment mechanism component is constant.

In one embodiment, the implant is configured to be implanted in a bodily lumen.

The male detachment mechanism component is configured to be reversibly attachable to the female detachment mechanism component.

The male detachment mechanism component is configured to be attachable and detachable from the female detachment mechanism component.

In a second aspect of the present disclosure, there is provided a delivery wire assembly having a female detachment mechanism component. The female detachment mechanism component comprises a coil configured to receive a male detachment mechanism component of an implant such that a male detachment mechanism component is attachable to the female detachment mechanism component.

The female detachment mechanism component of this aspect of the present disclosure has any of the features, or any combination of the features, of the female detachment mechanism component of the first aspect of the present disclosure and any of its embodiments, or any of the features described below.

In a third aspect of the present disclosure, there is provided an implant having a male detachment mechanism component configured to be received in a coil of a female detachment mechanism of a delivery wire assembly such that the male detachment mechanism component is attachable to the female detachment mechanism component.

The male detachment mechanism component of this aspect of the present disclosure has any of the features, or any combination of the features, of the male detachment mechanism component of the first aspect of the present disclosure and any of its embodiments, or any of the features described below.

BRIEF DESCRIPTION OF THE DRAWINGS

For a better understanding of the present disclosure, and to show how the same may be carried into effect, reference is made, by way of example only, to the following exemplary drawings, in which.

DETAILED DESCRIPTION

Figure 1:
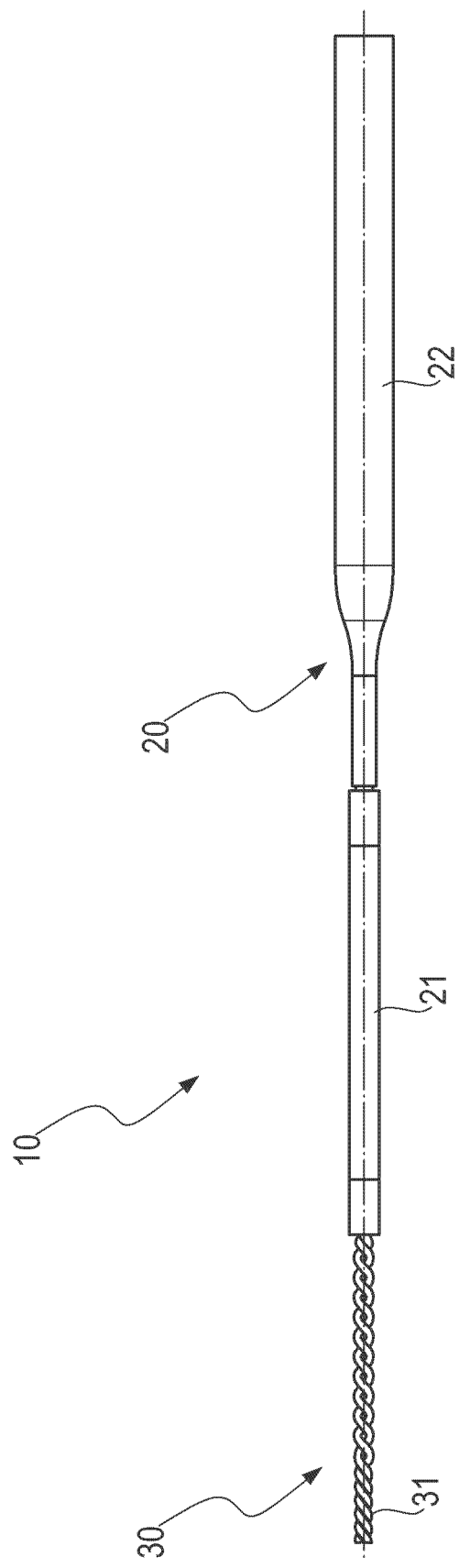
FIG. 1 shows an implant system according to an embodiment of the present disclosure.
Figure 2:
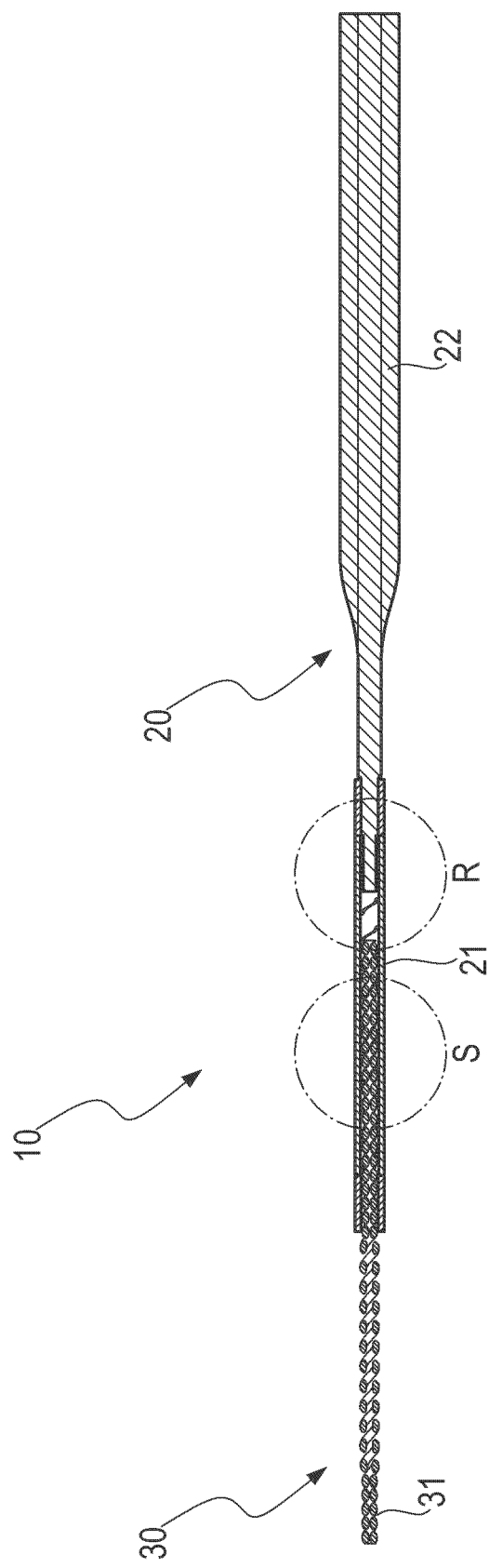
FIG. 2 shows a cross-section of the implant system shown in FIG. 1.

FIG. 1 shows an implant system 10 according to an embodiment of the present disclosure. FIG. 2 shows a cross-section of the implant system 10.

The implant system 10 comprises a delivery wire assembly 20 and an implant 30. Only parts of the delivery wire assembly 20 and the implant 30 are shown in the Figures.

The delivery wire assembly 20 has a female detachment mechanism component 21 comprising a coil 21*a*.

The implant 30 has a male detachment mechanism component 31, which may be part of the central core of the implant 30.

The implant 30 may be an implant configured for implantation within a bodily lumen. The implant 30 may be delivered to a desired location within the bodily lumen by the delivery wire assembly 20.

For example, the implant 30 may be an embolisation device for promoting clot formation in a bodily lumen. The implant 30 may have a contracted delivery configuration and an expanded deployed configuration. The implant 30 may comprise a stem. The implant 30 may comprise a plurality of flexible bristles extending radially outwardly from the stem. The plurality of flexible bristles may have a contracted delivery configuration and an expanded deployed configuration. The stem of the implant 30 may be connected to or be integral with the male detachment mechanism component 31.

The coil 21a is configured to receive the male detachment mechanism component 31 such that the male detachment mechanism component 31 is attachable to the female detachment mechanism component 21. The male detachment mechanism component 31 is attachable to the female detachment mechanism component 21 by a relative rotation in a first sense between the two components. The male detachment mechanism component is detachable from the female detachment mechanism component 21 by a relative rotation between the two components in the opposite sense.

The delivery wire assembly comprises a delivery wire 22.

When the male detachment mechanism component 31 is attached to the female detachment mechanism component 21, the delivery wire 22 may be manipulated to translate the implant 30 through a bodily lumen to the location to which it is supposed to be deployed. For example, the proximal end of the delivery wire 22 may be translated so as to effect a translation of the implant 30 through the bodily lumen. Once the implant 30 is in the correct location, the male detachment mechanism component 31 may be detached from the the female detachment mechanism component 21 by a relative rotation.

The male detachment mechanism component 31 may be formed from two wires being twisted along their length.

Figure 3:
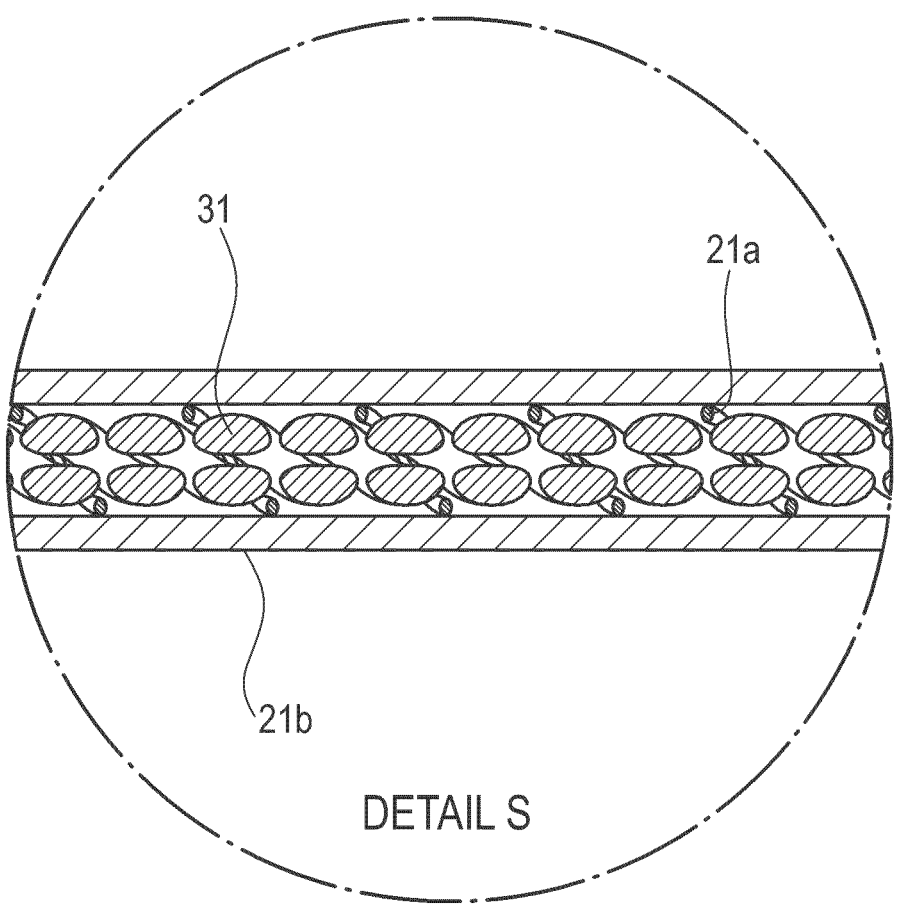
FIG. 3 shows the detail S of the cross-section of the implant system shown in FIG. 2.
Figure 4:
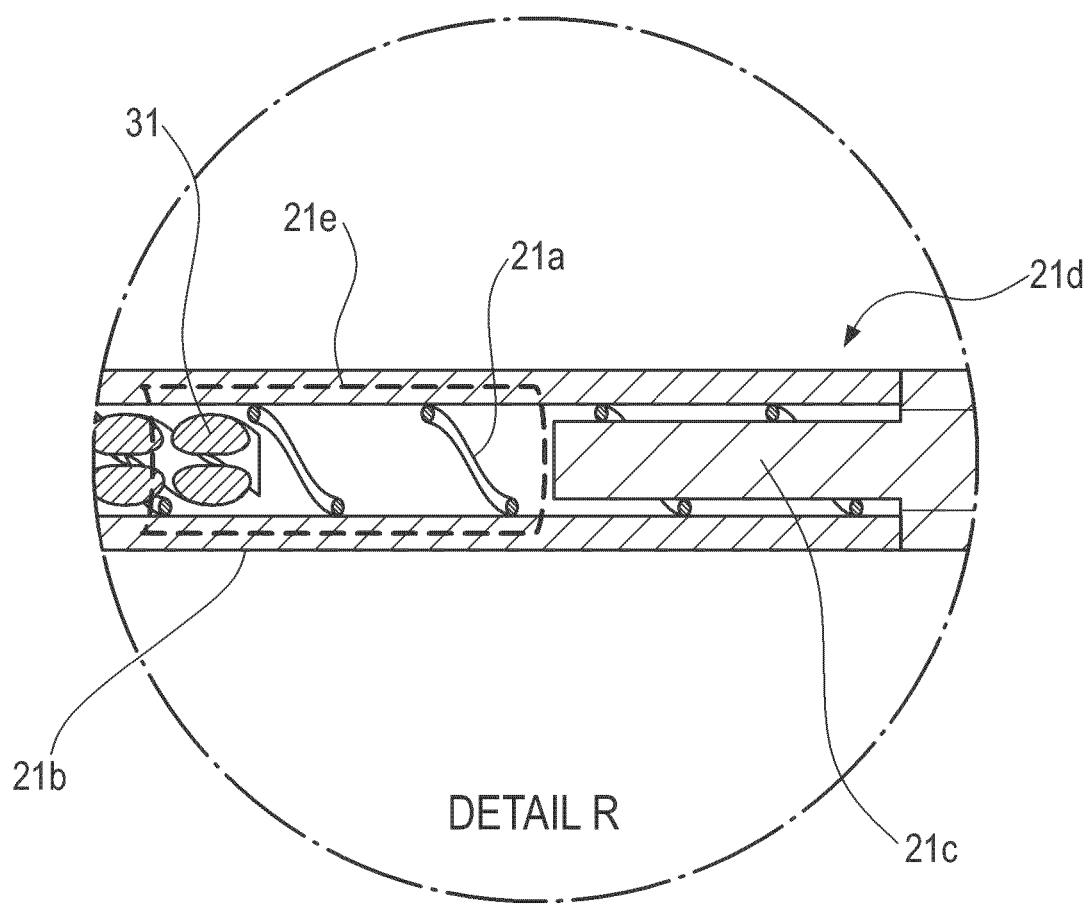
FIG. 4 shows the detail R of the cross-section of the implant system shown in FIG. 2.

FIG. 3 shows the detail S of the cross-section of the implant system 10 shown in FIG. 2. FIG. 4 shows the detail R of the cross-section of the implant system shown in FIG. 2.

The coil 21a may abut the surface of the internal bore of the cylinder 21b of the female detachment mechanism component 20 along the length of the coil 21a.

One end of the coil 21a may be fixed to the closed end 21d of the cylinder 21b. The coil 21a may be fixed to the closed end 21d of the cylinder 21b by glue and/or clamping.

The portion of the coil 21a which is not fixed is free to translate in along the length of the internal bore of the cylinder 21b. The portion of the coil 21a which is not fixed may translate by compressing or extending the free portion of the coil 21a.

The coil is fixed to the closed end of the cylinder 21b. The other end of the cylinder 21b is open so as to receive the male detachment mechanism component 31.

A portion of one end of the coil 21a is disposed over a mandrel 21c which extends from the closed end of the cylinder 21b.

As can be seen, the outer surface of the two wires twisted together (i.e. the male detachment mechanism 31) defines an external thread configured to mate with an internal thread formed by the coil 21a of the female detachment mechanism component 21.

The female detachment mechanism 21 may include a viewing window 21e. The viewing window 21e may be defined in the cylinder 21b of the female detachment mechanism 21. The viewing window 21e may be disposed along a portion of the cylinder 21b such that a user may be able to see the coil 21a and the male detachment mechanism component 31 disposed therein. The viewing window 21e may be configured to allow a user to view the internal bore of the cylinder 21b.

The viewing window 21e may be configured to allow a user to determine whether the male detachment mechanism 31 has been received within and/or is being removed from the female detachment mechanism 21. The viewing window 21e may be laser-cut into the cylinder 21b of the female detachment mechanism 21.

Figure 5:
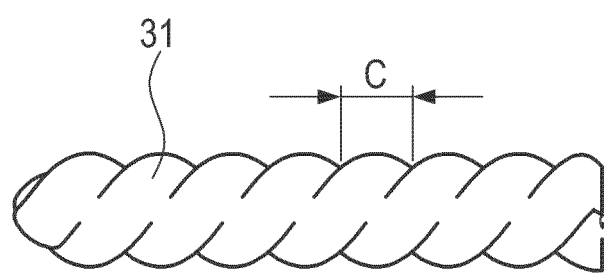
FIG. 5 shows an embodiment of a male detachment mechanism component.

FIG. 5 shows an embodiment of a male detachment mechanism component 31. The male detachment mechanism component 31 is formed by twisting two wires together along their length. The pitch C is shown in FIG. 5.

Although the above explanation is considered to fully clarify how the present disclosure may be straight-forwardly put into effect by those skilled in the art, it is to be regarded as purely exemplary. In particular, there are a number of variations which are possible, as may be appreciated by those skilled in the art.

For example, even though the above male detachment mechanism component 31 is formed by twisting two wires together, other embodiments are also compatible with the female detachment mechanism component 21.

For example, even though the above male detachment mechanism component 31 is formed by twisting two wires together, other embodiments are contemplated in which three or more wires are twisted together to form the male detachment mechanism component.

For example, even though the above female detachment mechanism component 21 includes a coil 21a for receiving the male detachment mechanism component 31, alternative embodiments are contemplated. For example, the female detachment mechanism component 21 may not include a coil 21a but rather has an internal thread created inside the cylinder 21b for receiving the male detachment mechanism component 31.

For example, the male detachment mechanism component 31 may be a coil. In some embodiments, the coil of the male detachment mechanism component is more tightly wound than the coil of the female detachment mechanism component 21.

All of the above are fully within the scope of the present disclosure, and are considered to form the basis for alternative embodiments in which one or more combinations of the above described features are applied, without limitation to the specific combinations disclosed above.

In light of this, there will be many alternatives which implement the teaching of the present disclosure. It is expected that one skilled in the art will be able to modify and adapt the above disclosure to suit its own circumstances and requirements within the scope of the present disclosure, while retaining some or all technical effects of the same, either disclosed or derivable from the above, in light of his common general knowledge in this art. All such equivalents, modifications or adaptions fall within the scope of the present disclosure.

The invention claimed is:

1. An implant system comprising:
   a delivery wire assembly having a female detachment mechanism component; and
   an implant having a male detachment mechanism component,
   wherein the female detachment mechanism component comprises a coil configured to receive the male detachment mechanism component such that the male detachment mechanism component is attachable to the female detachment mechanism component; wherein:

the female detachment mechanism component further comprises a cylinder defining an internal bore, and wherein the coil is disposed within the internal bore of the cylinder, and at least a portion of the coil is free to compress and extend a pitch of the coil along the length of the internal bore, and at least a portion of one end of the coil is disposed over a mandrel, the mandrel is within the portion of the coil and the coil extends beyond a distal end of the mandrel.

2. The implant system of claim 1, wherein the male detachment mechanism component is configured to be attached to the female detachment mechanism component by a relative rotation between the male detachment mechanism component and the female detachment mechanism component.

3. The implant system of claim 1, wherein the male detachment mechanism component comprises an external thread configured to mate with an internal thread formed by the coil of the female detachment mechanism component.

4. The implant system of claim 1, wherein the coil is a coil spring.

5. The implant system of claim 1, wherein the coil abuts the surface of the internal bore along at least a portion of the length of the coil, and, optionally, wherein the coil abuts the surface of the internal bore along the entire length of the coil.

6. The implant system of claim 1, wherein one end of the coil is fixed to the cylinder, and, optionally, wherein the one end of the coil is fixed to an end of the internal bore.

7. The implant system of claim 1, wherein the male detachment mechanism component comprises two wires twisted together.

8. The implant system of claim 7, wherein the outer surface of the two wires twisted together defines an external thread configured to mate with an internal thread formed by the coil of the female detachment mechanism component.

9. The implant system of claim 7, wherein the pitch of the coil of the female detachment mechanism component is an integer multiple of a pitch of the two wires twisted together and/or wherein the pitch of the coil of the female detachment mechanism component is one, two, three, four or five times the pitch of the two wires twisted together.

10. The implant system of claim 7, wherein the pitch of the two wires twisted together is constant and/or wherein the pitch of the coil of the female detachment mechanism component is constant.

11. The implant system of claim 7, wherein the two wires twisted together form a part of the core of the implant, and wherein the core is a central core of the implant.

12. The implant system of claim 7, wherein the handedness of the two wires twisted together is the same as the handedness of the coil of the female detachment mechanism component.

13. The implant system of claim 7, wherein the male detachment mechanism component comprises a coil.

14. The implant system of claim 13, wherein the outer surface of the coil defines an external thread configured to mate with an internal thread formed by the coil of the female detachment mechanism component.

15. The implant system of claim 13, wherein the handedness of the coil of the female detachment mechanism component is the same as the handedness of the coil of the male detachment mechanism component.

16. The implant system of claim 13, wherein a pitch of the coil of the female detachment mechanism component is an integer multiple of a pitch of the coil of the male detachment mechanism component and/or wherein a pitch of the coil of the female detachment mechanism component is one, two, three, four or five times the pitch of the coil of the male detachment mechanism component.

17. The implant system of claim 13, wherein the pitch of the coil of the male detachment mechanism component is constant and/or wherein the pitch of the coil of the female detachment mechanism component is constant.

18. The implant system of claim 1, wherein the implant is configured to be implanted in a bodily lumen.

* * * * *

UNITED STATES PATENT AND TRADEMARK OFFICE
CERTIFICATE OF CORRECTION

PATENT NO. : 11,583,286 B2
APPLICATION NO. : 16/638667
DATED : February 21, 2023
INVENTOR(S) : James Kehoe, Dónal McDonagh and John O'Shea It is certified that error appears in the above-identified patent and that said Letters Patent is hereby corrected as shown below:

On the Title Page

Item (54), and in the Specification, Column 1, Line 1, title, before "IMPLANT SYSTEM", insert --AN--.

Item (71), applicant, city, after "Clearstream Technologies Limited Enniscorthy", insert --, County Wexford--.

Item (72), inventor 1, city, after "James Kehoe, Enniscorthy", insert --County Wexford--.

Item (73), assignee, city, after "Clearstream Technologies Limited Enniscorthy", insert --, County Wexford--.

Signed and Sealed this
Fourth Day of April, 2023

Katherine Kelly Vidal
*Director of the United States Patent and Trademark Office*